US006702857B2

(12) United States Patent
Brauker et al.

(10) Patent No.: US 6,702,857 B2
(45) Date of Patent: Mar. 9, 2004

(54) MEMBRANE FOR USE WITH IMPLANTABLE DEVICES

(75) Inventors: James H. Brauker, San Diego, CA (US); Mark C. Shults, Madison, WI (US); Mark A. Tapsak, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 0 days.

(21) Appl. No.: 09/916,386

(22) Filed: Jul. 27, 2001

(65) Prior Publication Data

US 2003/0023317 A1 Jan. 30, 2003

(51) Int. Cl.[7] ................................ A61F 2/02; A61F 2/00
(52) U.S. Cl. ..................................... 623/23.76; 424/424
(58) Field of Search ........................... 623/23.76, 23.74, 623/23.73, 23.72, 23.71, 11.11, 16.11; 604/93.01; 424/424, 422, 423, 425

(56) References Cited

U.S. PATENT DOCUMENTS 4,353,888 A   10/1982   Sefton (List continued on next page.)

FOREIGN PATENT DOCUMENTS

| WO | WO 90/00738 | 1/1990 | |
| WO | WO 92/07525 | 5/1992 | |
| WO | WO9207525 A | 5/1992 | ............ A61F/2/00 |
| WO | WO 92/13271 | 8/1992 | |
| WO | WO 93/19701 | 10/1993 | |
| WO | WO 94/22367 | 10/1994 | |
| WO | WO 96/01611 | 1/1996 | |
| WO | WO 96/32076 | 10/1996 | |
| WO | WO 96/36296 | 11/1996 | |
| WO | WO9743633 A | 11/1997 | ......... G01N/27/327 |
| WO | WO0013003 A | 3/2000 | ......... G01N/21/64 |
| WO | WO0112158 A | 2/2001 | ............ A61K/9/02 |
| WO | WO 01/20019 | 3/2001 | |
| WO | WO 01/20334 | 3/2001 | |
| WO | WO 01/34243 | 5/2001 | |
| WO | WO0143660 A | 6/2001 | |
| WO | WO 01/58348 | 8/2001 | |
| WO | WO 01/68901 | 9/2001 | |
| WO | WO 01/69222 | 9/2001 | |
| WO | WO 01/88524 | 11/2001 | |
| WO | WO 01/88534 | 11/2001 | |

OTHER PUBLICATIONS

Sieminski, et al. *Biomaterials* 21 (2000) 2233–2241.
Results of Partial International Search for PCT Application No. PCT/US02/23902.
PCT International Search Report.

(List continued on next page.)

*Primary Examiner*—Corrine McDermott
*Assistant Examiner*—Alvin Stewart
(74) *Attorney, Agent, or Firm*—Knobbe Martens Olson & Bear LLP

(57) ABSTRACT

The present invention provides a biointerface membrane for use with an implantable device that interferes with the formation of a barrier cell layer including; a first domain distal to the implantable device wherein the first domain supports tissue attachment and interferes with barrier cell layer formation and a second domain proximal to the implantable device wherein the second domain is resistant to cellular attachment and is impermeable to cells. In addition, the present invention provides sensors including the biointerface membrane, implantable devices including these sensors or biointerface membranes, and methods of monitoring glucose levels in a host utilizing the analyte detection implantable device of the invention. Other implantable devices which include the biointerface membrane of the present invention, such as devices for cell transplantation, drug delivery devices, and electrical signal delivery or measuring devices are also provided.

43 Claims, 9 Drawing Sheets

U.S. PATENT DOCUMENTS

| | | | |
|---|---|---|---|
| 4,431,004 A | 2/1984 | Bessman et al. | |
| 4,436,094 A | 3/1984 | Cerami | |
| 4,453,537 A | 6/1984 | Spitzer | |
| 4,484,987 A | 11/1984 | Gough | |
| 4,686,044 A | 8/1987 | Behnke et al. | |
| 4,703,756 A | 11/1987 | Gough et al. | |
| 4,757,022 A | 7/1988 | Shults et al. | |
| 4,759,828 A | 7/1988 | Young et al. | |
| 4,787,398 A | 11/1988 | Garcia et al. | |
| 4,803,243 A | 2/1989 | Fujimoto et al. | |
| 4,823,808 A | 4/1989 | Clegg et al. | |
| 4,890,620 A | 1/1990 | Gough | |
| 4,902,294 A | 2/1990 | Gosserez | |
| 4,994,167 A | 2/1991 | Shults et al. | |
| 5,165,407 A | 11/1992 | Wilson et al. | |
| 5,190,041 A | 3/1993 | Palti | |
| 5,222,980 A * | 6/1993 | Gealow | 623/3 |
| 5,314,471 A | 5/1994 | Brauker et al. | |
| 5,321,414 A | 6/1994 | Alden et al. | |
| 5,322,063 A | 6/1994 | Allen et al. | |
| 5,344,454 A | 9/1994 | Clarkeet et al. | |
| 5,380,536 A | 1/1995 | Hubbell et al. | |
| 5,390,671 A | 2/1995 | Lord et al. | |
| 5,391,250 A | 2/1995 | Cheney, II et al. | |
| 5,417,395 A | 5/1995 | Fowler et al. | |
| 5,421,923 A | 6/1995 | Clarke et al. | |
| 5,431,160 A | 7/1995 | Wilkins | |
| 5,453,278 A | 9/1995 | Chan et al. | |
| 5,462,064 A | 10/1995 | D'Angelo et al. | |
| 5,469,846 A | 11/1995 | Khan | |
| 5,476,094 A | 12/1995 | Allen et al. | |
| 5,497,772 A | 3/1996 | Schulman et al. | |
| 5,538,511 A | 7/1996 | Van Antwerp | |
| 5,545,223 A | 8/1996 | Neuenfeldt et al. | |
| 5,549,675 A | 8/1996 | Neuenfeldt et al. | |
| 5,569,186 A | 10/1996 | Lord et al. | |
| 5,569,462 A | 10/1996 | Martinson et al. | |
| 5,578,463 A | 11/1996 | Berka et al. | |
| 5,584,876 A * | 12/1996 | Bruchman et al. | 623/1.44 |
| 5,593,440 A | 1/1997 | Brauker et al. | |
| 5,653,756 A | 8/1997 | Clarke et al. | |
| 5,660,163 A | 8/1997 | Schulman et al. | |
| 5,713,888 A | 2/1998 | Neuenfeldt et al. | |
| 5,733,336 A | 3/1998 | Neuenfeldt et al. | |
| 5,741,330 A | 4/1998 | Brauker et al. | |
| 5,777,060 A | 7/1998 | Van Antwerp | |
| 5,782,912 A | 7/1998 | Brauker et al. | |
| 5,787,900 A * | 8/1998 | Butler et al. | 128/898 |
| 5,800,529 A | 9/1998 | Brauker et al. | |
| 5,807,406 A | 9/1998 | Brauker et al. | |
| 5,882,354 A | 3/1999 | Brauker et al. | |
| 5,882,494 A * | 3/1999 | Van Antwerp | 204/403 |
| 5,913,998 A * | 6/1999 | Butler et al. | 156/245 |
| 5,964,261 A | 10/1999 | Neuenfeldt et al. | |
| 5,985,129 A | 11/1999 | Gough et al. | |
| 6,001,067 A * | 12/1999 | Shults et al. | 600/584 |
| 6,060,640 A * | 5/2000 | Pauley et al. | 623/23.72 |
| 6,122,536 A | 9/2000 | Sun et al. | |
| 6,144,869 A | 11/2000 | Berner et al. | |
| 6,175,752 B1 | 1/2001 | Say et al. | |
| 6,180,416 B1 | 1/2001 | Kurnik et al. | |
| 6,200,772 B1 | 3/2001 | Vadgama et al. | |
| 6,201,980 B1 | 3/2001 | Darrow et al. | |
| 6,208,894 B1 | 3/2001 | Schulman et al. | |
| 6,212,416 B1 | 4/2001 | Ward et al. | |
| 6,223,080 B1 | 4/2001 | Thompson | |
| 6,223,083 B1 | 4/2001 | Rosar | |
| 6,230,059 B1 | 5/2001 | Duffin | |
| 6,233,471 B1 | 5/2001 | Berner et al. | |
| 6,254,586 B1 | 7/2001 | Mann et al. | |
| 6,256,522 B1 | 7/2001 | Schultz | |
| 6,259,937 B1 | 7/2001 | Schulman et al. | |
| 6,272,364 B1 | 8/2001 | Kurnik | |
| 6,272,382 B1 | 8/2001 | Faltys et al. | |
| 6,299,578 B1 | 10/2001 | Kurnik et al. | |
| 6,309,351 B1 | 10/2001 | Kurnik et al. | |
| 6,326,160 B1 | 12/2001 | Dunn et al. | |
| 6,329,161 B1 | 12/2001 | Heller et al. | |

OTHER PUBLICATIONS

Updike et al., "Laboratory Evaluation of New Reusable Blood Glucose Sensor," *Diabetes Care*, 11:801–807 (1988).

Moatti–Sirat et al., "Towards Continuous Glucose Monitoring: In Vivo Evaluation of a Miniaturized Glucose Sensor Implanted for Several Days in Rat Subcutaneous Tissue," *Diabetologia* 35:224–30 (1992).

Armour et al., "Application of Chronic Intravascular Blood Glucose Sensor in Dogs," *Diabetes* 39:1519–26 (1990).

Woodward, "How Fibroblasts and Giant Cells Encapsulate Implants: Considerations in Design of Glucose Sensor," *Diabetes Care* 5:278–281 (1982).

Bindra et al., "Design and In Vitro Studies of a Needle–Type Glucose Sensor for Subcutaneous Monitoring," *Anal. Chem.* 63:1692–96 (1991).

Shults et al., "A Telemetry–Instrumentation System for Monitoring Multiple Subcutaneously Implanted Glucose Sensors," *IEEE Trans, Biomed. Eng.* 41:937–942 (1994).

Phillips and Smith, "Biomedical Applications of Polyurethanes: Implications of Failure Mechanisms," *J. Biomat. Appl.* 3:202–227 (1988).

Stokes, "Polyether Polyurethanes: Biostable or Not?," *J. Biomat. Appl.* 3:228–259 (1988).

Updike et al., "Enzymatic Glucose Sensors: Improved Long– Term Performance In Vitro and In Vivo," *Am.Soc. Artificial Internal Organs* 40:157–163 (1994).

Updike et al., "Implanting the Glucose Enzyme Electrode: Problems, Progress, and Alternative Solutions," *Diabetes Care* 5:207–21 (1982).

Rhodes et al., "Prediction of Pocket–Portable and Implantable Glucose Enzyme Electrode Performance from Combined Species Permeability and Digital Simulation Analysis," *Anal. Chem.* 66:1520–1529 (1994).

Tse and Gough, "Time–Dependent Inactivation of Immobilized Glucose Oxidase and Catalase," *Biotechnol. Bioeng.* 29:705–713 (1987).

Gilligan et al., "Evaluation of a Subcutaneous Glucose Sensor Out to 3 Months in a Dog Model," *Diabetes Care* 17:882–887 (1994).

McKean and Gough, "A Telemetry–Instrumentation System for Chronically Implanted Glucose and Oxygen Sensors," *IEEE Trans. Biomed. Eng.* 35:526–532 (1988).

Shichiri et al., "Telemetry Glucose Monitoring Device with Needle–Type Glucose Sensor—A Useful Tool for Blood Glucose Monitoring in Diabetic Individuals," *Diabetes Care* 9:298–301 (1986).

Lyman, "Polyurethanes. I. The Solution Polymerization of Diisocyanates with Ethylene Glycol," *J. Polymer Sci.* 45:49 (1960).

DuPont[1] Dimension AR® (Catalog).
Direct 30/30® meter (Markwell Medical) (Catalog).
Fischer et al., "Oxygen Tension at the Subcutaneous Implantation Site of Glucose Sensors," *Biomed. Biochem.* 11/12, 965–972 (1989).
Brauker et al., "Neovascularization of Sythetic Membranes Directed by Membrane Microarchitecture," *Journal of Biomedical Materials Research* 29:1517 (1995).

Abstract presented by James Brauker, Ph.D., "Neovascularization of Cell Transplantation Devices: Membrane Architecture–Driven and Implanted Tissue–Driven Vascularization," Baxter Healthcare Corp.
Brauker et al., "Local Inflammatory Response Around Diffusion Chambers Containing Xenografts", *Transplantation*, vol. 61, 1671–1677, No. 12, Jun. 27, 1996.

* cited by examiner

MEMBRANE FOR USE WITH IMPLANTABLE DEVICES

FIELD OF THE INVENTION

The present invention relates generally to biointerface membranes that may be utilized with implantable devices such as devices for the detection of analyte concentrations in a biological sample, cell transplantation devices, drug delivery devices and electrical signal delivering or measuring devices. The present invention further relates to methods for determining analyte levels using implantable devices including these membranes. More particularly, the invention relates to novel biointerface membranes, to sensors and implantable devices including these membranes, and to methods for monitoring glucose levels in a biological fluid sample using an implantable analyte detection device.

BACKGROUND OF THE INVENTION

One of the most heavily investigated analyte sensing devices is an implantable glucose sensor for detecting glucose levels in patients with diabetes. Despite the increasing number of individuals diagnosed with diabetes and recent advances in the field of implantable glucose monitoring devices, currently used devices are unable to provide data safely and reliably for long periods of time (e.g., months or years) [See, e.g., Moatti-Sirat et al., Diabetologia 35:224–30 (1992)]. There are two commonly used types of implantable glucose sensing devices. These types are those which are implanted intravascularly and those implanted in tissue.

With reference to devices that may be implanted in tissue, a disadvantage of these devices has been that they tend to lose their function after the first few days to weeks following implantation. At least one reason for this loss of function has been attributed to the fact that there is no direct contact with circulating blood to deliver sample to the tip of the probe of the implanted device. Because of these limitations, it has previously been difficult to obtain continuous and accurate glucose levels. However, this information is often extremely important to diabetic patients in ascertaining whether immediate corrective action is needed in order to adequately manage their disease.

Some medical devices, including implanted analyte sensors, drug delivery devices and cell transplantation devices require transport of solutes across the device-tissue interface for proper function. These devices generally include a membrane, herein referred to as a cell-impermeable membrane that encases the device or a portion of the device to prevent access by host inflammatory or immune cells to sensitive regions of the device.

A disadvantage of cell-impermeable membranes is that they often stimulate a local inflammatory response, called the foreign body response (FBR) that has long been recognized as limiting the function of implanted devices that require solute transport. Previous efforts to overcome this problem have been aimed at increasing local vascularization at the device-tissue interface with limited success.

The FBR has been well described in the literature and is composed of three main layers, as illustrated in FIG. 1. The innermost FBR layer 40, adjacent to the device, is composed generally of macrophages and foreign body giant cells 41 (herein referred to as the barrier cell layer). These cells form a monolayer 40 of closely opposed cells over the entire surface 48a of a smooth or microporous (<1.0 μm) membrane 48. The intermediate FBR layer 42 (herein referred to as the fibrous zone), lying distal to the first layer with respect to the device, is a wide zone (30–100 microns) composed primarily of fibroblasts 43 and fibrous matrix 44. The outermost FBR layer 46 is loose connective granular tissue containing new blood vessels 45 (herein referred to as the vascular zone 46). A consistent feature of the innermost layers 40 and 42 is that they are devoid of blood vessels. This has led to widely supported speculation that poor transport of molecules across the device-tissue interface 47 is due to a lack of vascularization near interface 47 (Scharp et al., World J. Surg. 8:221–229 (1984), Colton and Avgoustiniatos J. Biomech. Eng. 113:152–170 (1991)).

Patents by Brauker et al. (U.S. Pat. No. 5,741,330), and Butler et al. (U.S. Pat. No. 5,913,998), describe inventions aimed at increasing the number of blood vessels adjacent to the implant membrane (Brauker et al.), and growing within (Butler et al.) the implant membrane at the device-tissue interface. The patent of Shults et al. (U.S. Pat. No. 6,001,067) describes membranes that induce angiogenesis at the device-tissue interface of implanted glucose sensors. FIG. 2 illustrates a situation in which some blood vessels 45 are brought close to an implant membrane 48, but the primary layer 40 of cells adherent to the cell-impermeable membrane blocks glucose. This phenomenon is described in further detail below.

In the examples of Brauker et al. (supra), and Shults et al., bilayer membranes are described that have cell impermeable layers that are porous and adhesive to cells. Cells are able to enter into the interstices of these membranes, and form monolayers on the innermost layer, which is aimed at preventing cell access to the interior of the implanted device (cell impenetrable layers). Because the cell impenetrable layers are porous, cells are able to reach pseudopodia into the interstices of the membrane to adhere to and flatten on the membrane, as shown in FIGS. 1 and 2, thereby blocking transport of molecules across the membrane-tissue interface. The known art purports to increase the local vascularization in order to increase solute availability. However, the present studies show that once the monolayer of cells (barrier cell layer) is established adjacent to the membrane, increasing angiogenesis is not sufficient to increase transport of molecules such as glucose and oxygen across the device-tissue interface.

One mechanism of inhibition of transport of solutes across the device-tissue interface that has not been previously discussed in the literature is the formation of a uniform barrier to analyte transport by cells that form the innermost layer of the foreign body capsule. This layer of cells forms a monolayer with closely opposed cells having tight cell-to-cell junctions. When this barrier cell layer forms, it is not substantially overcome by increased local vascularization. Regardless of the level of local vascularization, the barrier cell layer prevents the passage of molecules that cannot diffuse through the layer. Again, this is illustrated in FIG. 2 where blood vessels 45 lie adjacent to the membrane but glucose transport is significantly reduced due to the impermeable nature of the barrier cell layer 40. For example, both glucose and its phosphorylated form do not readily transit the cell membrane and consequently little glucose reaches the implant membrane through the barrier layer cells.

It has been confirmed by the present inventors through histological examination of explanted sensors that the most likely mechanism for inhibition of molecular transport across the device-tissue interface is the barrier cell layer adjacent to the membrane. There is a strong correlation between desired device function and the lack of formation of a barrier cell layer at the device-tissue interface. In the present studies, devices that were observed histologically to have substantial barrier cell layers were functional only 41% of the time after 12 weeks in vivo. In contrast, devices that did not have significant barrier cell layers were functional 86% of the time after 12 weeks in vivo.

Consequently, there is a need for a membrane that interferes with the formation of a barrier layer and protects the sensitive regions of the device from host inflammatory response.

SUMMARY OF THE INVENTION

The biointerface membranes of the present invention interfere with the formation of a monolayer of cells adjacent to the membrane, henceforth referred to herein as a barrier cell layer, which interferes with the transport of oxygen and glucose across a device-tissue interface.

It is to be understood that various biointerface membrane architectures (e.g., variations of those described below) are contemplated by the present invention and are within the scope thereof.

In one aspect of the present invention, a biointerface membrane for use with an implantable device is provided including; a first domain distal to the implantable device wherein the first domain supports tissue ingrowth and interferes with barrier-cell layer formation and a second domain proximal to the implantable device wherein the second domain is resistant to cellular attachment and is impermeable to cells and cell processes.

In another aspect of the present invention, a biointerface membrane is provided including the properties of: promoting tissue ingrowth into; interfering with barrier cell formation on or within; resisting barrier-cell attachment to; and blocking cell penetration into the membrane.

In yet another aspect, a sensor head for use in an implantable device is provided which includes a biointerface membrane of the present invention.

In other aspects, a sensor for use in an implantable device that measures the concentration of an analyte in a biological fluid is provided including the biointerface membrane of the present invention.

In still another aspect of the present invention, a device for measuring an analyte in a biological fluid is provided, the device including the biointerface membrane of the present invention, a housing which includes electronic circuitry, and at least one sensor as provided above operably connected to the electronic circuitry of the housing.

The present invention further provides a method of monitoring analyte levels including the steps of: providing a host, and an implantable device as provided above; and implanting the device in the host. In one embodiment, the device is implanted subcutaneously.

Further provided by the present invention is a method of measuring analyte in a biological fluid including the steps of: providing i) a host, and ii) a implantable device as provided above capable of accurate continuous analyte sensing; and implanting the device in the host. In one embodiment of the method, the device is implanted subcutaneously.

In still another aspect of the present invention, an implantable drug delivery device is provided including a biointerface membrane as provided above. Preferably the implantable drug delivery device is a pump, a microcapsule or a macrocapsule.

The present invention further provides a device for implantation of cells which includes a biointerface membrane as provided above.

Also encompassed by the present invention is an electrical pulse delivering or measuring device, including a biointerface membrane according to that provided above.

The biointerface membranes, devices including these membranes and methods of use of these membranes provided by the invention allow for long term protection of implanted cells or drugs, as well as continuous information regarding, for example, glucose levels of a host over extended periods of time. Because of these abilities, the biointerface membranes of the present invention can be extremely important in the management of transplant patients, diabetic patients and patients requiring frequent drug treatment.

Definitions

In order to facilitate an understanding of the present invention, a number of terms are defined below.

The terms "biointerface membrane," and the like refer to a permeable membrane that functions as a device-tissue interface comprised of two or more domains. Preferably, the biointerface membrane is composed of two domains. The first domain supports tissue ingrowth, interferes with barrier cell layer formation and includes an open cell configuration having cavities and a solid portion. The second domain is resistant to cellular attachment and impermeable to cells (e.g., macrophages). The biointerface membrane is made of biostable materials and may be constructed in layers, uniform or non-uniform gradients (i.e. anisotropic), or in a uniform or non-uniform cavity size configuration.

The term "domain" refers to regions of the biointerface membrane that may be layers, uniform or non-uniform gradients (e.g. anisotropic) or provided as portions of the membrane.

The term "barrier cell layer" refers to a cohesive monolayer of closely opposed cells (e.g. macrophages and foreign body giant cells) that may adhere to implanted membranes and interfere with the transport of molecules across the membrane.

The phrase "distal to" refers to the spatial relationship between various elements in comparison to a particular point of reference. For example, some embodiments of a device include a biointerface membrane having an cell disruptive domain and a cell impermeable domain. If the sensor is deemed to be the point of reference and the cell disruptive domain is positioned farther from the sensor, then that domain is distal to the sensor.

The term "proximal to" refers to the spatial relationship between various elements in comparison to a particular point of reference. For example, some embodiments of a device include a biointerface membrane having a cell disruptive domain and a cell impermeable domain. If the sensor is deemed to be the point of reference and the cell impermeable domain is positioned nearer to the sensor, then that domain is proximal to the sensor.

The term "cell processes" and the like refers to pseudopodia of a cell.

The term "solid portions" and the like refer to a material having a structure that may or may not have an open-cell configuration, but in either case prohibits whole cells from traveling through or residing within the material.

The term "substantial number" refers to the number of linear dimensions within a domain (e.g. pores or solid portions) in which greater than 50 percent of all dimensions are of the specified size, preferably greater than 75 percent and, most preferably, greater than 90 percent of the dimensions have the specified size.

The term "co-continuous" and the like refers to a solid portion wherein an unbroken curved line in three dimensions exists between any two points of the solid portion.

The term "biostable" and the like refers to materials that are relatively resistant to degradation by processes that are encountered in vivo.

The term "sensor" refers to the component or region of a device by which an analyte can be quantitated.

The term "analyte" refers to a substance or chemical constituent in a biological fluid (e.g., blood or urine) that is intended to be analyzed. A preferred analyte for measurement by analyte detection devices including the biointerface membranes of the present invention is glucose.

The terms "operably connected," "operably linked," and the like refer to one or more components being linked to another component(s) in a manner that allows transmission of signals between the components. For example, one or more electrodes may be used to detect the amount of analyte in a sample and convert that information into a signal; the signal may then be transmitted to an electronic circuit means. In this case, the electrode is "operably linked" to the electronic circuitry.

The term "electronic circuitry" refers to the components of a device required to process biological information obtained from a host. In the case of an analyte measuring device, the biological information is obtained by a sensor regarding a particular analyte in a biological fluid, thereby providing data regarding the amount of that analyte in the fluid. U.S. Pat. Nos. 4,757,022, 5,497,772 and 4,787,398 describe suitable electronic circuit means that may be utilized with devices including the biointerface membrane of the present invention.

The phrase "member for determining the amount of glucose in a biological sample" refers broadly to any mechanism (e.g., enzymatic or non-enzymatic) by which glucose can be quantitated. For example, some embodiments of the present invention utilize a membrane that contains glucose oxidase that catalyzes the conversion of oxygen and glucose to hydrogen peroxide and gluconate: Glucose+$O_2$=Gluconate+$H_2O_2$. Because for each glucose molecule metabolized, there is a proportional change in the co-reactant $O_2$ and the product $H_2O_2$, one can monitor the current change in either the co-reactant or the product to determine glucose concentration.

The term "host" refers generally to mammals, particularly humans.

The term "accurately" means, for example, 90% of measured glucose values are within the "A" and "B" region of a standard Clarke error grid when the sensor measurements are compared to a standard reference measurement. It is understood that like any analytical device, calibration, calibration validation and recalibration are required for the most accurate operation of the device.

The phrase "continuous glucose sensing" refers to the period in which monitoring of plasma glucose concentration is continuously performed, for example, about every 10 minutes.

DETAILED DESCRIPTION OF THE INVENTION

Figure 1:
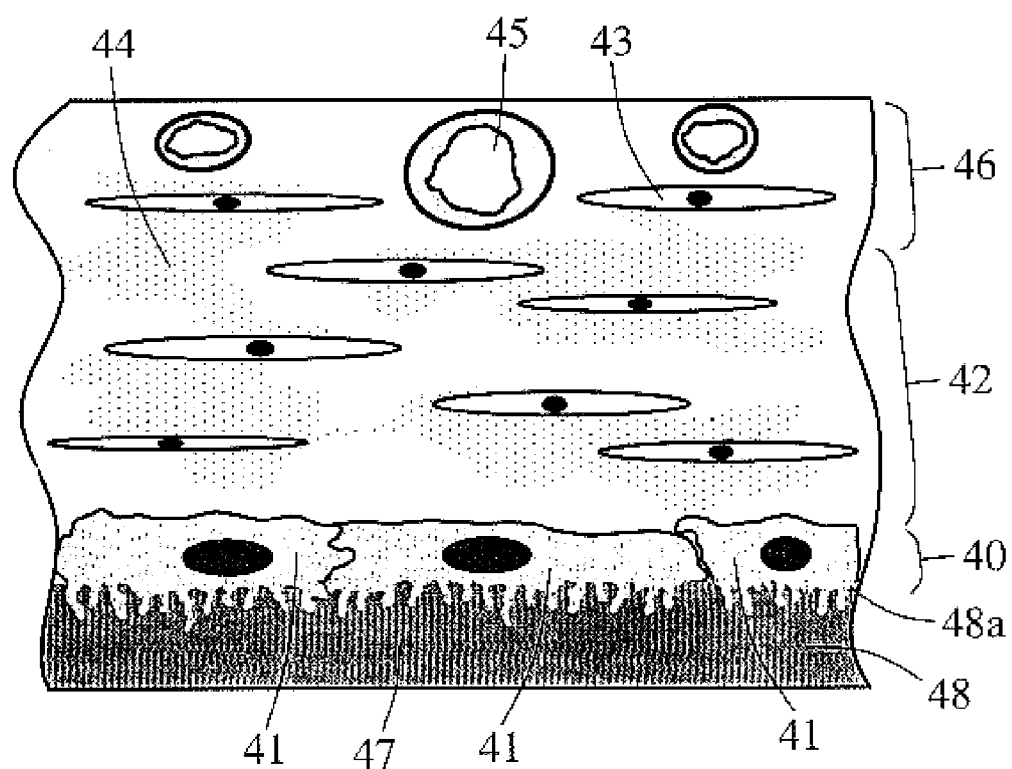
FIG. 1 is an illustration of classical three-layered foreign body response to a synthetic membrane implanted under the skin.
Figure 2:
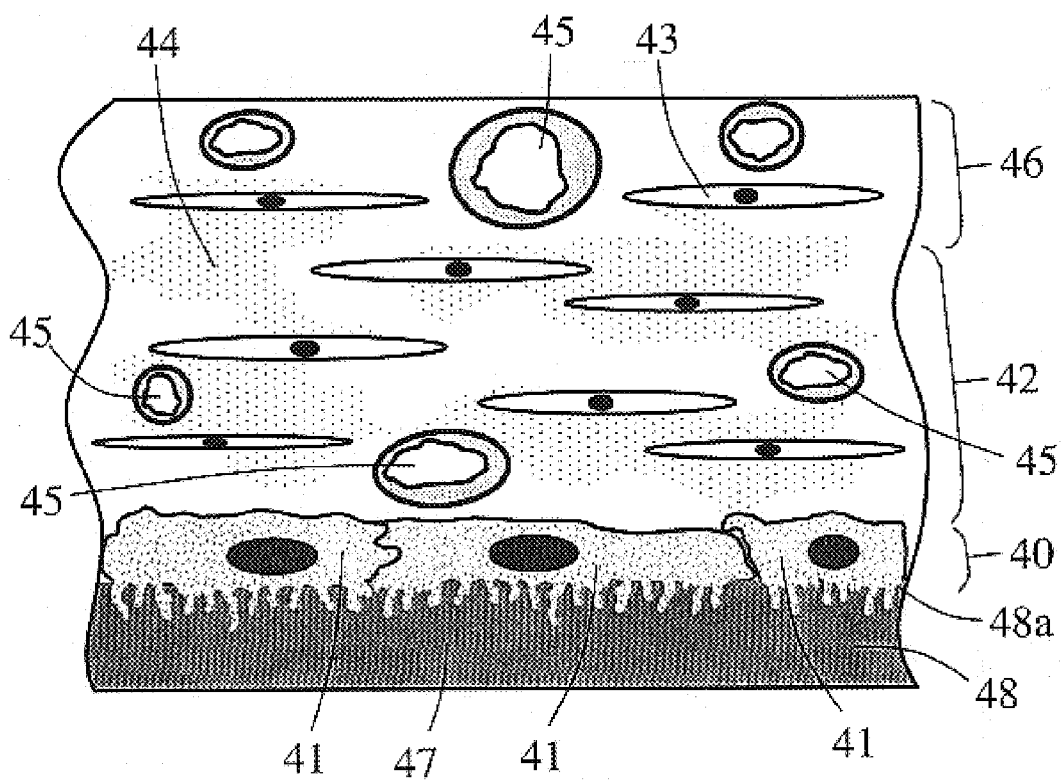
FIG. 2 is an illustration of a device having increased neovascularization within the intermediary layer of the foreign body response.

The present invention relates generally to novel biointerface membranes, their uses with implantable devices and methods for determining analyte levels in a biological fluid. More particularly, the invention provides biointerface membranes that may be utilized with implantable devices and methods for monitoring and determining glucose levels in a biological fluid, a particularly important measurement for individuals having diabetes.

Although the description that follows is primarily directed at glucose monitoring devices including the biointerface membranes of the present invention and methods for their use, these biointerface membranes are not limited to use in devices that measure or monitor glucose. Rather, these biointerface membranes may be applied to a variety of devices, including for example, those that detect and quantify other analytes present in biological fluids (including, but not limited to, cholesterol, amino acids and lactate), especially those analytes that are substrates for oxidase enzymes [see, e.g., U.S. Pat. No. 4,703,756 to Gough et al., hereby incorporated by reference] cell transplantation devices (U.S. Pat. Nos.: 6,015,572, 5,964,745 and 6,083,523), drug delivery devices (U.S. Pat. Nos.: 5,458,631, 5,820,589 and 5,972, 369) and electrical delivery and/or measuring devices such as implantable pulse generation cardiac pacing devices (U.S. Pat. Nos.: 6,157,860, 5,782,880 and 5,207,218), electrocardiogram device (U.S. Pat. Nos. 4,625,730 and 5,987,352) and electrical nerve stimulating devices (U.S. Pat. Nos. 6,175,767, 6,055,456 and 4,940,065).

Implantable devices for detecting analyte concentrations in a biological system may utilize the biointerface membranes of the present invention to interfere with the formation of a barrier cell layer, thereby assuring that the sensor receives analyte concentrations representative of that in the vasculature. Drug delivery devices may utilize the biointerface membranes of the present invention to protect the drug housed within the device from host inflammatory or immune cells that might potentially damage or destroy the drug. In addition, the biointerface membrane prevents the formation of a barrier cell layer that might interfere with proper dispensing of drug from the device for treatment of the host. Correspondingly, cell transplantation devices may utilize the biointerface membranes of the present invention to protect the transplanted cells from attack by the host inflammatory or immune response cells while simultaneously allowing nutrients as well as other biologically active molecules needed by the cells for survival to diffuse through the membrane.

The materials contemplated for use in preparing the biointerface membrane also eliminate or significantly delay biodegradation. This is particularly important for devices that continuously measure analyte concentrations. For example, in a glucose-measuring device, the electrode surfaces of the glucose sensor are in contact with (or operably connected with) a thin electrolyte phase, which in turn is covered by a membrane that contains an enzyme, e.g., glucose oxidase, and a polymer system. The biointerface membrane covers this enzyme membrane and serves, in part, to protect the sensor from external forces and factors that may result in biodegradation. By significantly delaying biodegradation at the sensor, accurate data may be collected over long periods of time (e.g. months to years). Correspondingly, biodegradation of the biointerface membrane of implantable cell transplantation devices and drug delivery devices could allow host inflammatory and immune cells to enter these devices, thereby compromising long-term function.

Devices and probes that are implanted into subcutaneous tissue will almost always elicit a foreign body capsule (FBC) as part of the body's response to the introduction of a foreign material. Therefore, implantation of a glucose sensor results in an acute inflammatory reaction followed by building of fibrotic tissue. Ultimately, a mature FBC including primarily a vascular fibrous tissue forms around the device (Shanker and Greisler, Inflammation and Biomaterials in Greco RS, ed. Implantation Biology: The Host Response and Biomedical Devices, pp68–80, CRC Press (1994)).

In general, the formation of a FBC has precluded the collection of reliable, continuous information because it was previously believed to isolate the sensor of the implanted device in a capsule containing fluid that did not mimic the levels of analytes (e.g. glucose and oxygen) in the body's vasculature. Similarly, the composition of a FBC has prevented stabilization of the implanted device, contributing to motion artifact that also renders unreliable results. Thus, conventionally, it has been the practice of those skilled in the art to attempt to minimize FBC formation by, for example, using a short-lived needle geometry or sensor coatings to minimize the foreign body reaction.

In contrast to conventionally known practice, the teachings of the present invention recognize that FBC formation is the dominant event surrounding long-term implantation of any sensor and must be managed to support rather than hinder or block sensor performance. It has been observed that during the early periods following implantation of an analyte-sensing device, particularly a glucose sensing device, glucose sensors function well. However, after a few days to two or more weeks of implantation, these device lose their function. For example, U.S. Pat. No. 5,791,344 and Gross et al. Performance Evaluation of the Minimed Continuous Monitoring System During Patient home Use", Diabetes Technology and Therapuetics, Vol 2 Number 1, pp49–56, 2000 have reported a glucose oxidase sensor (that has been approved for use in humans by the Food and Drug Administration) that functioned well for several days following implantation but loses function quickly after 3 days. We have observed similar device behavior with our implantable sensor. These results suggest that there is sufficient vascularization and, therefore, perfusion of oxygen and glucose to support the function of an implanted glucose sensor for the first few days following implantation. New blood vessel formation is clearly not needed for the function of a glucose oxidase mediated electrochemical sensor implanted in the subcutaneous tissue for at least several days after implantation.

We have observed that this lack of sensor function after several days is most likely due to cells, such as polymorphonuclear cells and monocytes that migrate to the wound site during the first few days after implantation. These cells consume glucose and oxygen. If there is an overabundance of such cells, they may deplete the glucose and/or oxygen before it is able to reach the sensor enzyme layer, therefore reducing the sensitivity of the device or rendering it non-functional. After the first few days, further inhibition of device function may be due to cells that associate with the membrane of the device and physically block the transport of glucose into the device (i.e. barrier cells). Increased vascularization would not be expected to overcome barrier cell blockage. The present invention contemplates the use of particular biointerface membrane architectures that interfere with barrier cell layer formation on the membrane's surface. The present invention also contemplates the use of these membranes with a variety of implantable devices (e.g. analyte measuring devices, particularly glucose measuring devices, cell transplantation devices, drug delivery devices and electrical signal delivery and measuring devices).

The sensor interface region refers to the region of a monitoring device responsible for the detection of a particular analyte. For example, in some embodiments of a glucose-monitoring device, the sensor interface refers to that region where a biological sample contacts (directly or after passage through one or more membranes or layers) an enzyme (e.g., glucose oxidase). The sensor interface region may include a biointerface membrane according to the present invention having different domains and/or layers that can cover and protect an underlying enzyme membrane and the electrodes of an implantable analyte-measuring device. In general, the biointerface membranes of the present invention prevent direct contact of the biological fluid sample with the sensor. The membranes only permit selected substances (e.g., analytes) of the fluid to pass therethrough for reaction in the immobilized enzyme domain. The biointerface membranes of the present invention are biostable and prevent barrier cell formation. The characteristics of this biointerface membrane are now discussed in more detail.

I. Biointerface Membrane

Figure 3:
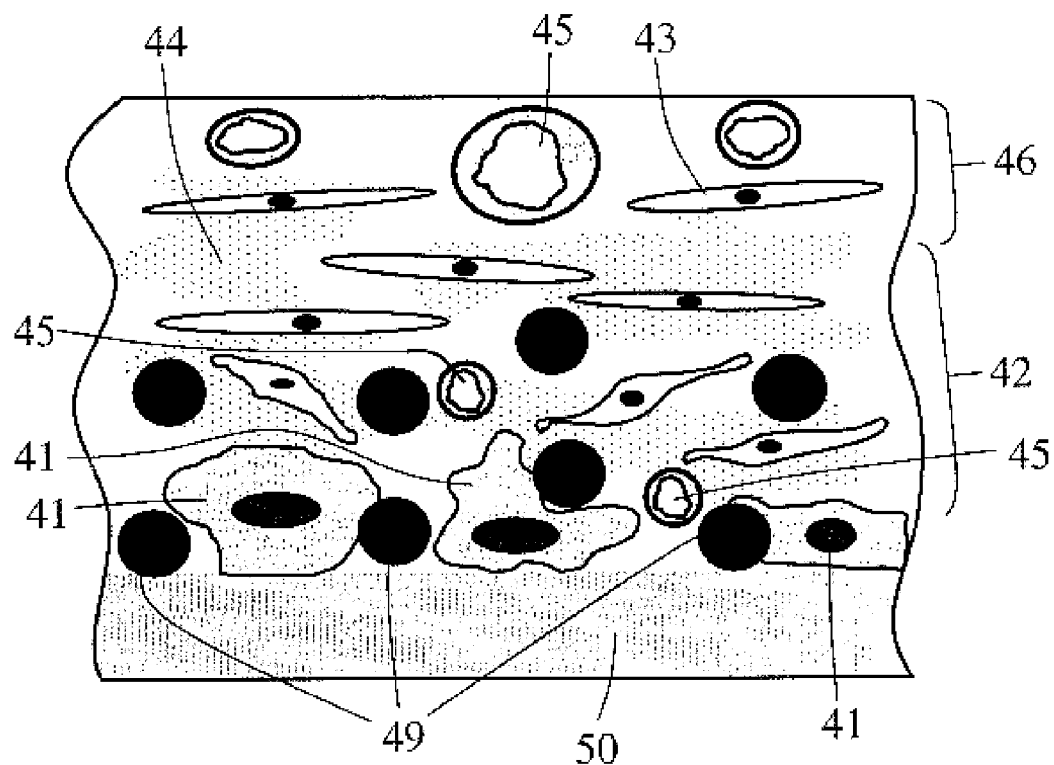
FIG. 3 is an illustration of a membrane of the present invention including a barrier-cell disruptive domain composed of fibers and a cell impermeable domain.

The biointerface membrane is constructed of two or more domains. Referring now to FIG. 3, preferably, the membrane includes a cell impermeable domain 50 proximal to an implantable device, also referred to as the second domain; and a cell disruptive domain, which in the embodiment illustrated includes non-woven fibers 49 distal to an implantable device, also referred to as the first domain.

A. Barrier-Cell Disruptive (First) Domain

Figure 4:
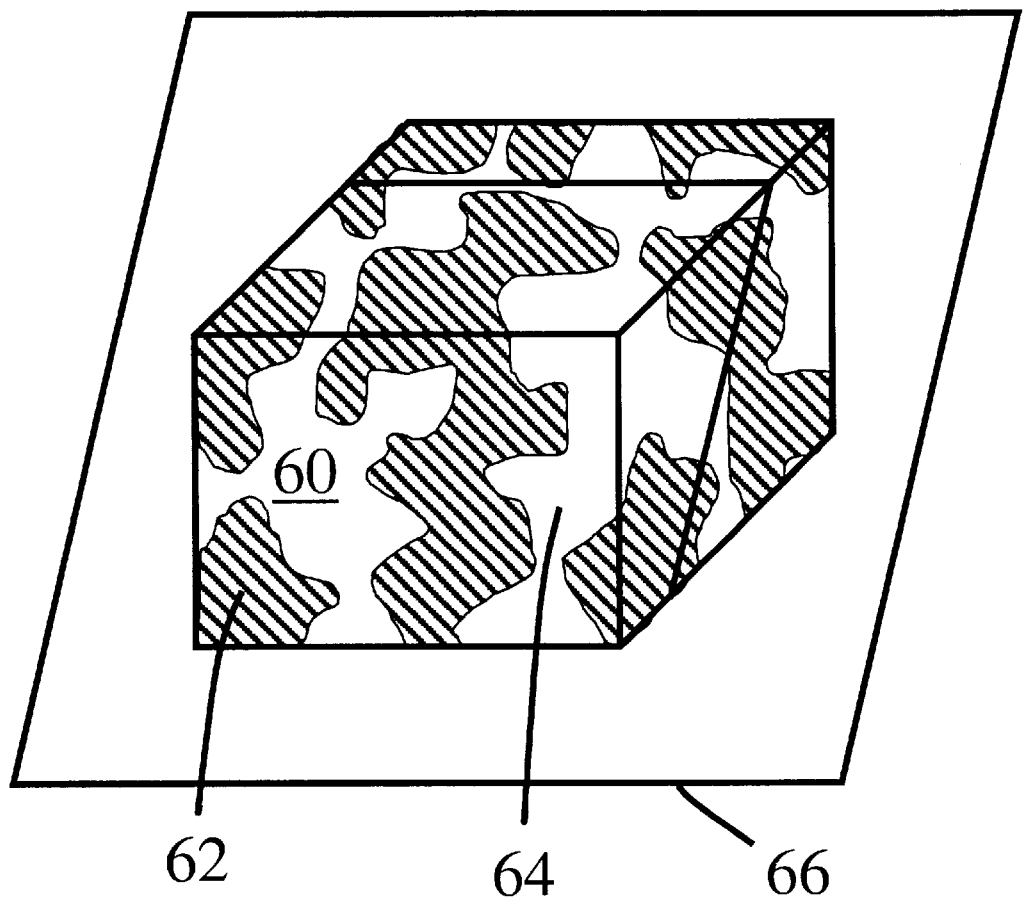
FIG. 4 is an illustration of a three dimensional section of the first domain showing the solid portions and cavities.

As described above, the outermost domain of the inventive membrane includes a material that supports tissue ingrowth. The barrier-cell disruptive domain may be composed of an open-cell configuration having cavities and solid portions. For example, FIG. 4 is an illustration of a three dimensional section 60 of a barrier-cell disruptive domain having solid portions 62 and cavities 64. Cells may enter into the cavities, however, they can not travel through or wholly exist within the solid portions. The cavities allow most substances to pass through, including, e.g., macrophages.

The open-cell configuration yields a co-continuous solid domain that contains greater than one cavity in three dimensions substantially throughout the entirety of the membrane. In addition, the cavities and cavity interconnections may be formed in layers having different cavity dimensions.

Figure 5:
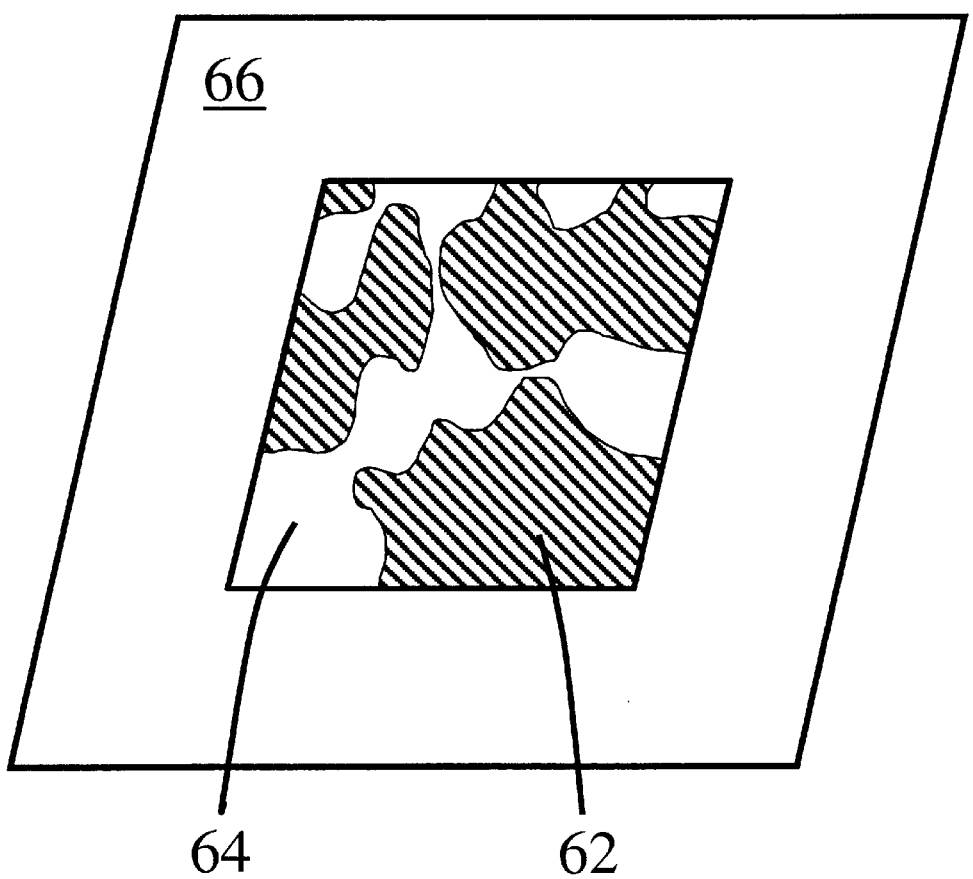
FIG. 5 is an illustration of a cross-section of the first domain in FIG. 4 showing solid portions and cavities.

In order to better describe the dimensions of cavities and solid portions, a two dimensional plane 66 cut through the barrier-cell disruptive domain can be utilized (FIG. 5). A dimension across a cavity 64 or solid portion 62 can be described as a linear line. The length of the linear line is the distance between two points lying at the interface of the cavity and solid portion. In this way, a substantial number of the cavities are not less than 20 microns in the shortest dimension and not more than 1000 microns in the longest dimension. Preferably, a substantial number of the cavities are not less than 25 microns in the shortest dimension and not more than 500 microns in the longest dimension.

Furthermore, the solid portion has not less than 5 microns in a substantial number of the shortest dimensions and not more than 2000 microns in a substantial number of the longest dimensions. Preferably, the solid portion is not less than 10 microns in a substantial number of the shortest dimensions and not more than 1000 microns in a substantial number of the longest dimensions and, most preferably, not less than 10 microns in a substantial number of the shortest dimensions and not more than 400 microns in a substantial number of the longest dimensions.

The solid portion may be comprised of polytetrafluoroethylene or polyethyleneco-tetrafluoroethylene. Preferably, the solid portion includes polyurethanes or block copolymers and, most preferably, is comprised of silicone.

In desired embodiments, the solid portion is composed of porous silicone or non-woven fibers. Non-woven fibers are preferably made from polyester or polypropylene. For example, FIG. 3 illustrates how the non-woven fibers 49 serve to disrupt the continuity of cells, such that they are not able to form a classical foreign body response. All the cell types that are involved in the formation of a FBR may be present. However, they are unable to form an ordered closely opposed cellular monolayer parallel to the surface of the device as in a typical foreign body response to a smooth surface. In this example, the 10-micron dimension provides a suitable surface for foreign body giant cells, but the fibers are in such proximity to allow and foster in growth of blood vessels 45 and vascularize the biointerface region (FIG. 3). Devices with smaller fibers have been used in previous inventions, but such membranes are prone to delamination due to the forces applied by cells in the interstices of the membrane. After delamination, cells are able to form barrier layers on the smooth or microporous surface of the bioprotective layer if it is adhesive to cells or has pores of sufficient size for physical penetration of cell processes, but not of whole cells.

When non-woven fibers are utilized as the solid portion of the present invention, the non-woven fibers may be greater than 5 microns in the shortest dimension. Preferably, the non-woven fibers are about 10 microns in the shortest dimension and, most preferably, the non-woven fibers are greater than or equal to 10 microns in the shortest dimension.

The non-woven fibers may be constructed of polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones, and block copolymers thereof including, for example, di-block, tri-block, alternating, random and graft copolymers (block copolymers are discussed in U.S. Pat. Nos. 4,803,243 and 4,686,044, hereby incorporated by reference). Preferably, the non-woven fibers are comprised of polyolefins or polyester or polycarbonates or polytetrafluoroethylene. The thickness of the cell disruptive domain is not less than about 20 microns and not more than about 2000 microns.

B. Cell Impermeable (Second) Domain

The inflammatory response that initiates and sustains a FBC is associated with disadvantages in the practice of sensing analytes. Inflammation is associated with invasion of inflammatory response cells (e.g. macrophages) which have the ability to overgrow at the interface forming barrier cell layers which may block transport across the biointerface membrane. These inflammatory cells may also biodegrade many artificial biomaterials (some of which were, until recently, considered nonbiodegradable). When activated by a foreign body, tissue macrophages degranulate, releasing from their cytoplasmic myeloperoxidase system hypochlorite (bleach) and other oxidative species. Hypochlorite and other oxidative species are known to break down a variety of polymers. However, polycarbonate based polyurethanes are believed to be resistant to the effects of these oxidative species and have been termed biodurable. In addition, because hypochlorite and other oxidizing species are short-lived chemical species in vivo, biodegradation will not occur if macrophages are kept a sufficient distance from the enzyme active membrane.

The present invention contemplates the use of cell impermeable biomaterials of a few microns thickness or more (i.e., a cell impermeable domain) in most of its membrane architectures. Desirably, the thickness of the cell impermeable domain is not less than about 10 microns and not more than about 100 microns. This domain of the biointerface membrane is permeable to oxygen and may or may not be permeable to glucose and is constructed of biodurable materials (e.g. for period of several years in vivo) that are impermeable by host cells (e.g. macrophages) such as, for example, polymer blends of polycarbonate based polyurethane and PVP.

The innermost domain of the inventive membrane is non-adhesive for cells (i.e. the cell impermeable domain), which is in contrast to the inventions of Brauker et al. (supra), and Shults et al. (supra). In both of these previous patents, examples are provided in which the cellimpenetrable membrane (Brauker et al.) or biointerface membrane (Shults et al.) are derived from a membrane known as Biopore™ as a cell culture support sold by Millipore (Bedford, Mass.). In the presence of certain extracellular matrix molecules, and also in vivo, many cell types are able to strongly adhere to this membrane making it incapable of serving as a non-adhesive domain. Further, since they allow adherence of cells to the innermost layer of the membrane they promote barrier cell layer formation that decreases the membranes ability to transport molecules across the device-tissue interface. Moreover, when these cells multiply, they ultimately cause pressure between the membrane layers resulting in delamination of the layers and catastrophic failure of the membrane.

As described above, in one embodiment of the inventive membrane, the second domain is resistant to cellular attachment and is impermeable to cells and preferably composed of a biostable material. The second domain may be formed from materials such as those previously listed for the first domain and as copolymers or blends with hydrophilic polymers such as polyvinylpyrrolidone (PVP), polyhydroxyethyl methacrylate, polyvinylalcohol, polyacrylic acid, polyethers, such as polyethylene glycol, and block copolymers thereof including, for example, di-block, tri-block, alternating, random and graft copolymers (block copolymers are discussed in U.S. Pat. Nos. 4,803,243 and 4,686,044, hereby incorporated by reference).

Preferably, the second domain is comprised of a polyurethane and a hydrophilic polymer. Desirably, the hydrophilic polymer is polyvinylpyrrolidone. In one embodiment of this aspect of the invention, the second domain is polyurethane comprising not less than 5 weight percent polyvinylpyrrolidone and not more than 45 weight percent polyvinylpyrrolidone. Preferably, the second domain comprises not less than 20 weight percent polyvinylpyrrolidone and not more than 35 weight percent polyvinylpyrrolidone and, most preferably, polyurethane comprising about 27 weight percent polyvinylpyrrolidone.

As described above, in one desired embodiment the cell impermeable domain is comprised of a polymer blend comprised of a non-biodegradable polyurethane comprising polyvinylpyrrolidone. This prevents adhesion of cells in vitro and in vivo and allows many molecules to freely diffuse through the membrane. However, this domain prevents cell entry or contact with device elements underlying the membrane, and prevents the adherence of cells, and thereby prevents the formation of a barrier cell layer.

II. Implantable Glucose Monitoring Devices Using the Biointerface Membranes of the Present Invention The present invention contemplates the use of unique membrane architectures around the sensor interface of an implantable device. However, it should be pointed out that the present invention does not require a device including particular electronic components (e.g., electrodes, circuitry, etc). Indeed, the teachings of the present invention can be used with virtually any monitoring device suitable for implantation (or subject to modification allowing implantation); suitable devices include, analyte measuring devices, cell transplantation devices, drug delivery devices, electrical signal delivery and measurement devices and other devices such as those described in U.S. Pat. Nos. 4,703,756 and 4,994,167 to Shults et al.; U.S. Pat. No. 4,703,756 to Gough et al., and U.S. Pat. No. 4,431,004 to Bessman et al.; the contents of each being hereby incorporated by reference, and Bindra et al., Anal. Chem. 63:1692–96 (1991).

Figure 6A:
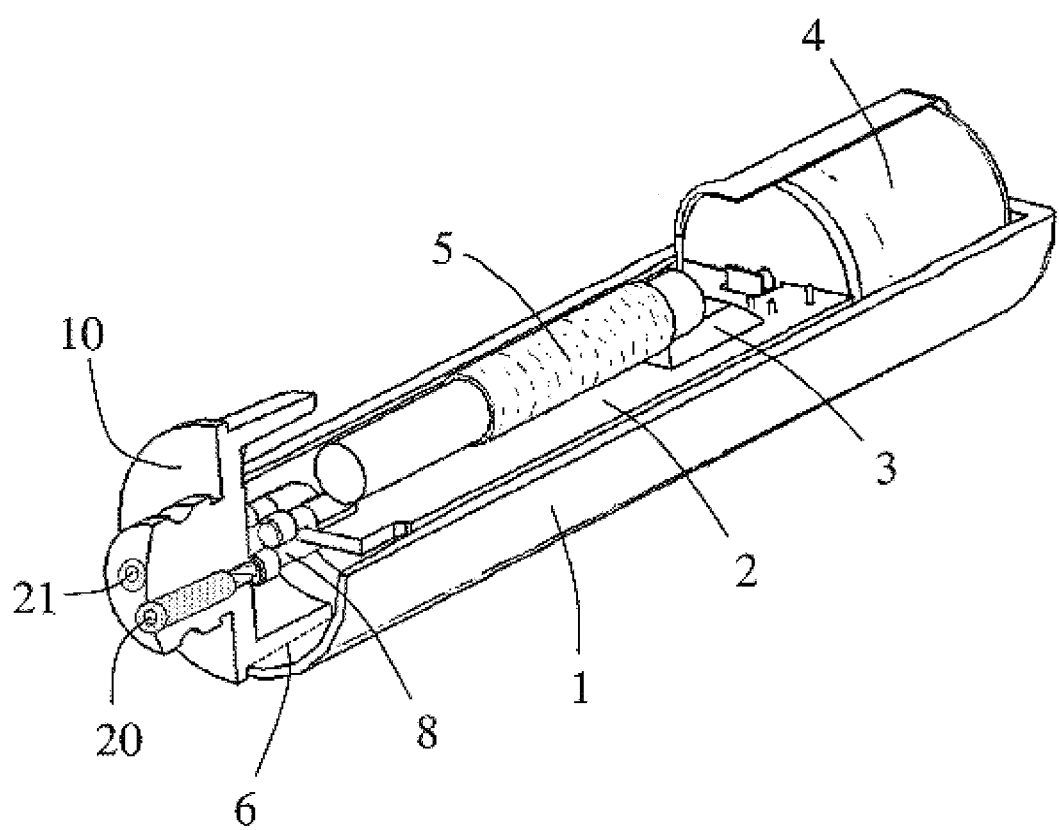
FIG. 6A depicts a cross-sectional drawing of one embodiment of an implantable analyte measuring device for use in combination with a membrane according to the present invention.

We refer now to FIG. 6A, which shows a preferred embodiment of an analyte measuring device for use in combination with a membrane according to the present invention. In this embodiment, a ceramic body 1 and ceramic head 10 houses the sensor electronics that include a circuit board 2, a microprocessor 3, a battery 4, and an antenna 5. Furthermore, the ceramic body 1 and head 10 possess a matching taper joint 6 that is sealed with epoxy. The electrodes are subsequently connected to the circuit board via a socket 8.

Figure 6B:
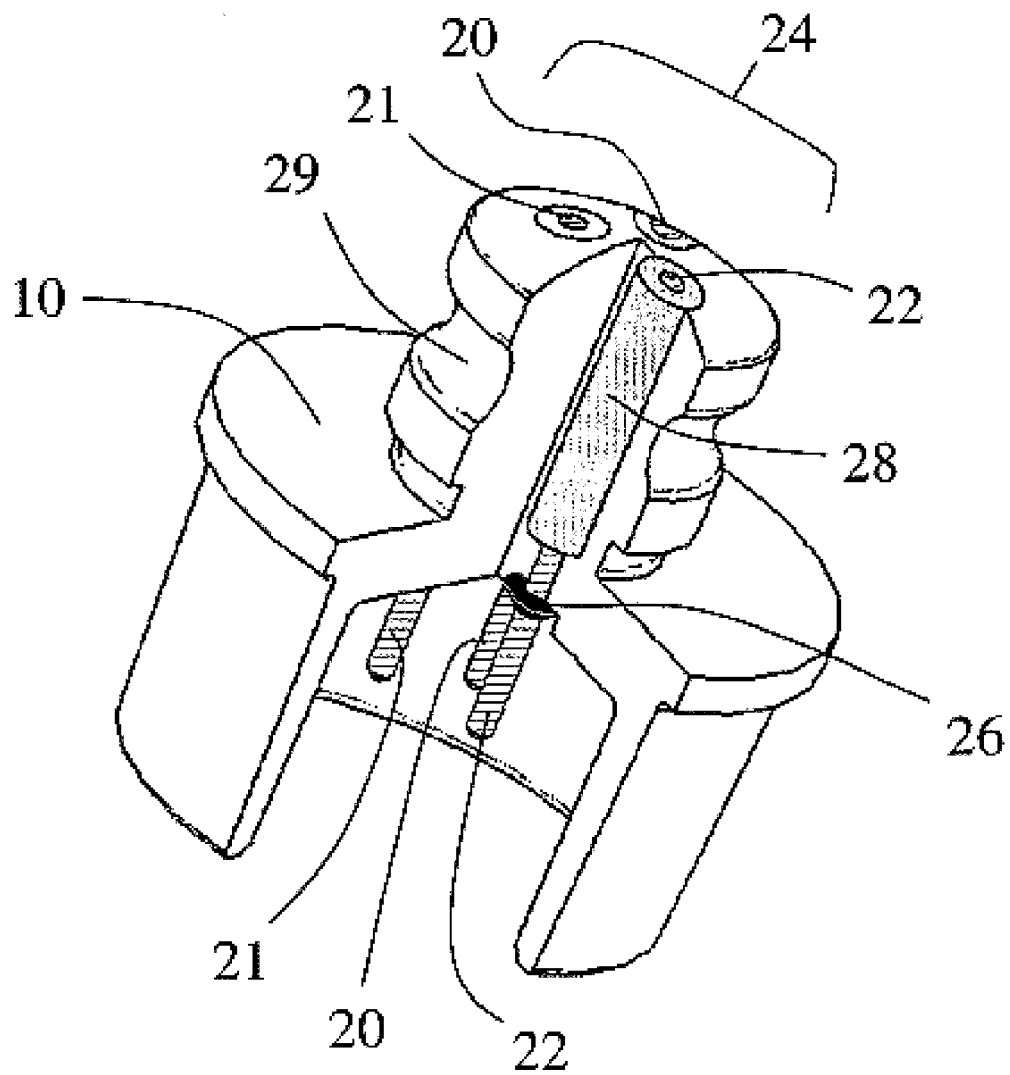
FIG. 6B depicts a cross-sectional exploded view of the sensor head shown in FIG. 6A.

As indicated in detail in Fig. 6B, three electrodes protrude through the ceramic head 10, a platinum working electrode 21, a platinum counter electrode 22 and a silver/silver chloride reference electrode 20. Each of these is hermetically brazed 26 to the ceramic head 10 and further affixed with epoxy 28. The sensing region 24 is covered with the sensing membrane described below and the ceramic head 10 contains a groove 29 so that the membrane may be affixed into place with an o-ring.

Figure 6C:
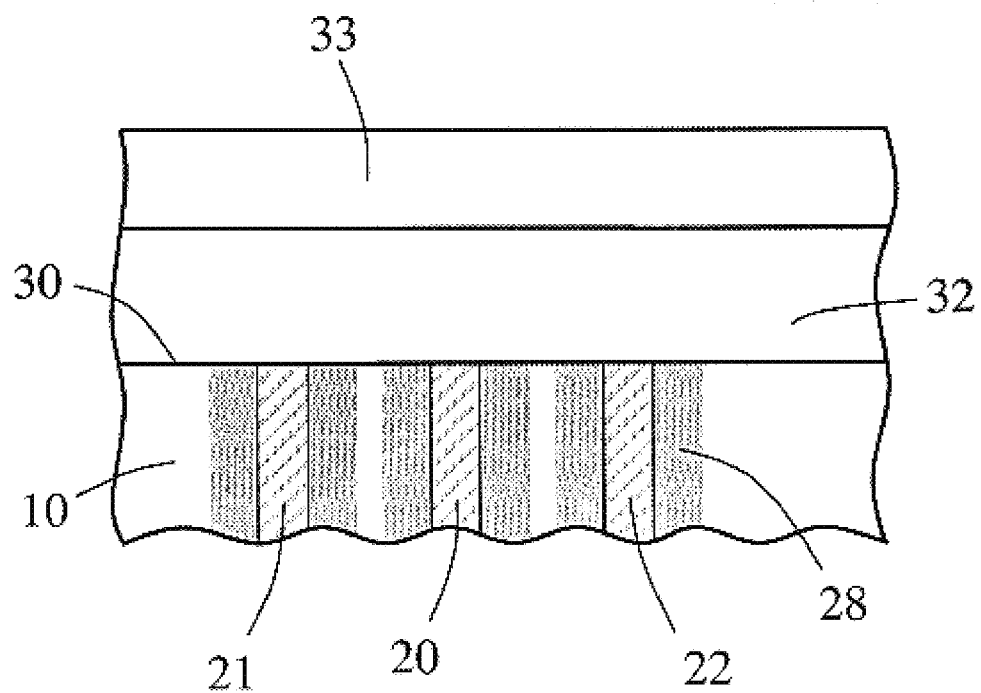
FIG. 6C depicts a cross-sectional exploded view of the electrode-membrane region set forth in FIG. 6B.

FIG. 6C depicts a cross-sectional exploded view of the electrode-membrane region 24 set forth in FIG. 6B detailing the sensor tip and the functional membrane layers. As depicted in FIG. 6C, the electrode-membrane region includes the inventive biointerface membrane 33 and a sensing membrane 32. The top ends of the electrodes are in contact with the electrolyte phase 30, a free-flowing fluid phase. The electrolyte phase is covered by the sensing membrane 32 that includes an enzyme, e.g., glucose oxidase. In turn, the inventive interface membrane 33 covers the enzyme membrane 32 and serves, in part, to protect the sensor from external forces that may result in environmental stress cracking of the sensing membrane 32.

III Experimental

The following examples serve to illustrate certain preferred embodiments and aspects of the present invention and are not to be construed as limiting the scope thereof In the preceding description and the experimental disclosure which follows, the following abbreviations apply: Eq and Eqs (equivalents); mEq (milliequivalents); M (molar); mM (millimolar) $\mu$M (micromolar); N (Normal); mol (moles); mmol (millimoles); $\mu$mol (micromoles); nmol (nanomoles); g (grams); mg (milligrams); $\mu$g (micrograms); Kg (kilograms); L (liters); mL (milliliters); dL (deciliters); $\mu$L (microliters); cm (centimeters); mm (millimeters); $\mu$m (micrometers); nm (nanometers); h and hr (hours); min. (minutes); s and sec. (seconds); ° C. (degrees Centigrade); Astor Wax (Titusville, Pa.); BASF Wyandotte Corporation (Parsippany, N.J.); Data Sciences, Inc. (St. Paul, Minn.); Douglas Hansen Co., Inc. (Minneapolis, Minn.); DuPont (DuPont Co., Wilmington, Del.); Exxon Chemical (Houston, Tex.); GAF Corporation (New York, N.Y.); Markwell Medical (Racine, Wis.); Meadox Medical, Inc. (Oakland, N.J.); Mobay (Mobay Corporation, Pittsburgh, Pa.); Sandoz (East Hanover, N.J.); and Union Carbide (Union Carbide Corporation; Chicago, Ill.).

EXAMPLE 1

Preparation of Biointerface Membrane with Non-Woven Fibers

The barrier-cell disruptive domain may be prepared from a non-woven polyester fiber filtration membrane. The cell-impermeable domain may then be coated on this domain layer. The cell-impermeable domain was prepared by placing approximately 706 gm of dimethylacetamide (DMAC) into a 3L stainless steel bowl to which a polycarbonateurethane solution (1325 g, Chronoflex AR 25% solids in DMAC and a viscosity of 5100 cp) and polyvinylpyrrolidone (125 g, Plasdone K-90D) were added. The bowl was then fitted to a planetary mixer with a paddle type blade and the contents were stirred for 1 hour at room temperature. This solution was then coated on the barrier-cell disruptive domain by knife-edge drawn at a gap of 0.006" and dried at 60° C. for 24 hours. The membrane is then mechanically secured to the sensing device by an O-ring.

EXAMPLE 2

Preparation of Biointerface Membrane with Porous Silicone

The barrier-cell disruptive domain can be comprised of a porous silicone sheet. The porous silicone was purchased from Seare Biomatrix Systems, Inc. The cell-impermeable domain was prepared by placing approximately 706 gm of dimethylacetamide (DMAC) into a 3L stainless steel bowl to which a polycarbonateurethane solution (1,325 gm, Chronoflex AR 25% solids in DMAC and a viscosity of 5100 cp) and polyvinylpyrrolidone (125 gm, Plasdone K-90D) were added. The bowl was then fitted to a planetary mixer with a paddle type blade and the contents were stirred for 1 hour at room temperature. The cell-impermeable domain coating solution was then coated onto a PET release liner (Douglas Hansen Co.) using a knife over roll set at a 0.012" gap. This film was then dried at 305° F. The final film was approximately 0.0015" thick. The biointerface membrane was prepared by pressing the porous silicone onto the cast cell-impermeable domain. The membrane is then mechanically secured to the sensing device by an O-ring.

EXAMPLE 3

Test Method for Glucose Measuring Device Function

In vivo sensor function was determined by correlating the sensor output to blood glucose values derived from an external blood glucose meter. We have found that non-diabetic dogs do not experience rapid blood glucose changes, even after ingestion of a high sugar meal. Thus, a 10% dextrose solution was infused into the sensor-implanted dog. A second catheter is placed in the opposite leg for the purpose of blood collection. The implanted sensor was programmed to transmit at 30-second intervals using a pulsed electromagnet. A dextrose solution was infused at a rate of 9.3 ml/minute for the first 25 minutes, 3.5 ml/minute for the next 20 minutes, 1.5 ml/minute for the next 20 minutes, and then the infusion pump was powered off Blood glucose values were measured in duplicate every five minutes on a blood glucose meter (LXN Inc., San Diego, Calif.) for the duration of the study. A computer collected the sensor output. The data was then compiled and graphed in a spreadsheet, time aligned, and time shifted until an optimal R-squared value was achieved. The R-squared value reflects how well the sensor tracks with the blood glucose values.

EXAMPLE 4

In Vivo Evaluation of Glucose Measuring Devices Including the Biointerface Membranes of the Present Invention To test the importance of a cell-disruptive membrane, implantable glucose sensors comprising the biointerface membranes of the present invention were implanted into dogs in the subcutaneous tissues and monitored for glucose response on a weekly basis. Control devices comprising only a cell-impermeable domain ("Control") were compared with devices comprising a cell-impermeable domain and a barrier-cell disruptive domain, in particular, wherein the barrier-cell disruptive domain was either a non-woven fiber ("Non-Woven Fibers") or porous silicone ("Porous Silicone").

Figure 7:
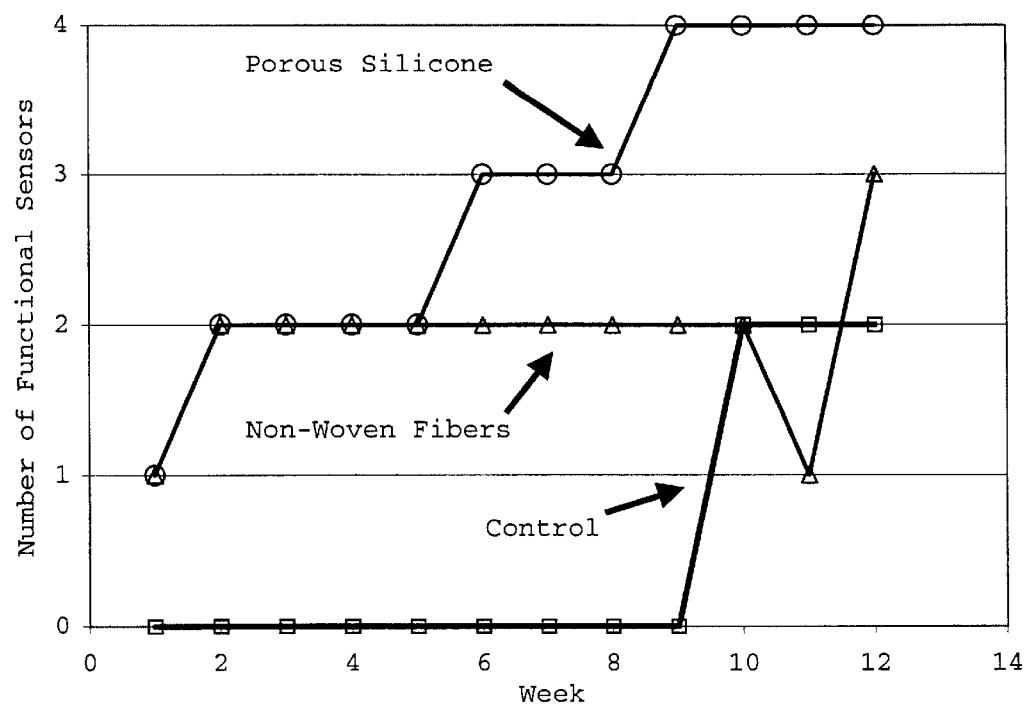
FIG. 7 is a graphical representation of the number of functional sensors versus time (i.e. weeks) comparing control devices including only a cell-impermeable domain ("Control"), with devices including a cell-impermeable domain and a barrier-cell domain, in particular, wherein the barrier-cell disruptive domain includes non-woven fiber ("Non-Woven Fibers") and wherein the barrier-cell disruptive domain includes porous silicone ("Porous Silicone").

Four devices from each condition were implanted subcutaneously in the ventral abdomen of normal dogs. On a weekly basis, the dogs were infused with glucose as described in Example 3 in order to increase their blood glucose levels from about 120 mg/dl to about 300 mg/dl. Blood glucose values were determined with a LXN blood glucose meter at 5-minute intervals. Sensor values were transmitted at 0.5-minute intervals. Regression analysis was done between blood glucose values and the nearest sensor value within one minute. Devices that yielded an R-squared value greater than 0.5 were considered functional. FIG. 7 shows, for each condition, the number of functional devices over the 12-week period of the study. Both test devices performed better than the control devices over the first 9 weeks of the study. All of the porous silicone devices were functional by week 9. Two of 4 polypropylene fiber devices were functional by week 2, and 3 of 4 were functional on week 12. In contrast, none of the control devices were functional until week 10, after which 2 were functional for the remaining 3 weeks. These data clearly show that the use of a cell-disruptive layer in combination with a cell-impermeable layer improves the function of implantable glucose sensors.

The description and experimental materials presented above are intended to be illustrative of the present invention while not limiting the scope thereof It will be apparent to those skilled in the art that variations and modifications can be made without departing from the spirit and scope of the present invention.

What is claimed is:

1. A biointerface membrane for use with an implantable device comprising;
   a) a first domain distal to said implantable device wherein said first domain supports tissue ingrowth and interferes with barrier-cell layer formation and
   b) a second domain proximal to said implantable device wherein said second domain is resistant to cellular attachment and is impermeable to cells and cell processes.

2. A biointerface membrane according to claim 1 wherein said first domain is comprised of an open-cell configuration having cavities and a solid portion.

3. A biointerface membrane according to claim 2 wherein said open-cell configuration comprises a depth of greater than one cavity in three dimensions substantially throughout the entirety of the domain.

4. A biointerface membrane according to claim 2 wherein a substantial number of said cavities are not less than 20 microns in the shortest dimension and not more than 1000 microns in the longest dimension.

5. A biointerface membrane according to claim 2 wherein a substantial number of said cavities are not less than 25 microns in the shortest dimension and not more than 500 microns in the longest dimension.

6. A biointerface membrane according to claim 2 wherein said cavities and cavity interconnections are formed in layers having different cavity dimensions.

7. A biointerface membrane according to claim 2 wherein said solid portion has not less than 5 microns in a substantial number of the shortest dimensions and not more than 2000 microns in a substantial number of the longest dimensions.

8. A biointerface membrane according to claim 2 wherein said solid portion has not less than 10 microns in a substantial number of the shortest dimensions and not more than 1000 microns in a substantial number of the longest dimensions.

9. A biointerface membrane according to claim 2 wherein said solid portion has not less than 10 microns in a substantial number of the shortest dimensions and not more than 400 microns in a substantial number of the longest dimensions.

10. A biointerface membrane according to claim 2 wherein said solid portion comprises silicone.

11. A biointerface membrane according to claim 2 wherein said solid portion comprises polyurethanes.

12. A biointerface membrane according to claim 2 wherein said solid portion comprises block copolymers.

13. A biointerface membrane according to claim 2 wherein said solid portion is made of a material selected from the group consisting of polytetrafluoroethylene, polyethylene-co-tetrafluoroethylene, polyolefins, polyesters, and polycarbonates.

14. A biointerface membrane according to claim 2 wherein said solid portion comprises non-woven fibers.

15. A biointerface membrane according to claim 14 wherein said solid portion is comprised of non-woven fibers greater than 5 microns in the shortest dimension.

16. A biointerface membrane according to claim 14 wherein said solid portion is comprised of non-woven fibers of about 10 microns in the shortest dimension.

17. A biointerface membrane according to claim 14 wherein said solid portion is comprised of non-woven fibers greater than or equal to 10 microns in the shortest dimension.

18. A biointerface membrane according to claim 14 wherein said solid portion is comprised of non-woven fibers greater than 10 microns in the shortest dimension.

19. A biointerface membrane according to claim 14 wherein said solid portion is comprised of polytetrafluoro ethylene.

20. A biointerface membrane according to claim 14 wherein said solid portion is comprised of polyolefins.

21. A biointerface membrane according to claim 14 wherein said solid portion is comprised of polyesters.

22. A biointerface membrane according to claim 14 wherein said solid portion is comprised of polycarbonates.

23. A biointerface membrane according to claim 1 wherein said second domain is composed of a biostable material.

24. A biointerface membrane according to claim 23 wherein said biostable material is comprised of a polyurethane and a hydrophilic polymer.

25. A biointerface membrane according to claim 23 wherein said biostable material is polyurethane comprising polyvinylpyrrolidone.

26. A biointerface membrane according to claim 23 wherein said second domain is polyurethane comprising not less than 5 weight percent polyvinylpyrrolidone and not more than 45 weight percent polyvinylpyrrolidone.

27. A biointerface membrane according to claim 23 wherein said second domain is polyurethane comprising not less than 20 weight percent polyvinylpyrrolidone and not more than 35 weight percent polyvinylpyrrolidone.

28. A biointerface membrane according to claim 23 wherein said second domain is polyurethane comprising about 27 weight percent polyvinylpyrrolidone.

29. A sensor head for use in an implantable device comprising a biointerface membrane according to claim 1.

30. An implantable device for measuring an analyte in a biological fluid, comprising:
   a) a housing comprising electronic circuitry; and
   b) at least one sensor head according to claim 29 operably connected to said electronic circuit means of said housing.

31. A method of monitoring analyte levels, comprising:
   a) providing i) a host, and ii) an implantable device according to claim 30, and
   b) implanting said device in said host.

32. A method according to claim 31, wherein said implanting is subcutaneous.

33. A method of measuring analyte in a biological fluid, comprising:
   a) providing i) a host, and ii) an implantable device according to claim 30 capable of accurate continuous analyte sensing; and
   b) implanting said device in said host.

34. A method according to claim 33, wherein said implanting is subcutaneous.

35. An implantable device according to claim 30, wherein said sensor head further comprises a member for determining the amount of glucose in a biological sample.

36. An analyte measuring device comprising a biointerface membrane according to claim 1.

37. A cell transplantation device comprising a biointerface membrane according to claim 1.

38. A drug delivery device comprising a biointerface membrane according to claim 1.

39. An implantable drug delivery device according to claim 38 wherein said drug delivery device is selected from the group consisting of a pump, a microcapsule and a macrocapsule.

40. An electrical signal measuring device comprising a biointerface membrane according to claim 1.

41. An electrical pulse delivering device comprising a biointerface membrane according to claim 1.

42. A biointerface membrane, wherein said membrane comprises a first domain and a second domain, the membrane comprising the properties of:
   a) promoting tissue ingrowth into said first domain;
   b) interfering with barrier cell formation on or within said first domain;
   c) resisting barrier cell attachment to said second domain; and
   d) blocking cell penetration into said second domain.

43. A biointerface membrane comprising a first domain and a second domain in combination that are adapted to:
   a) permit tissue ingrowth into said first domain;
   b) interfere with barrier cell formation on or within said first domain;
   c) resist baffler cell attachment to said second domain; and
   d) block cell penetration into said second domain.

* * * * *

(12) EX PARTE REEXAMINATION CERTIFICATE (8426th)
United States Patent
Brauker et al.

(10) Number: US 6,702,857 C1
(45) Certificate Issued: Jul. 26, 2011

(54) MEMBRANE FOR USE WITH IMPLANTABLE DEVICES

(75) Inventors: James H. Brauker, San Diego, CA (US); Mark C. Shults, Madison, WI (US); Mark A. Tapsak, San Diego, CA (US)

(73) Assignee: Dexcom, Inc., San Diego, CA (US)

Reexamination Request:
No. 90/011,067, Jun. 25, 2010

Reexamination Certificate for:
Patent No.: 6,702,857
Issued: Mar. 9, 2004
Appl. No.: 09/916,386
Filed: Jul. 27, 2001

(51) Int. Cl.
*A61F 2/02* (2006.01)
*A61F 2/00* (2006.01)

(52) U.S. Cl. .................................. 623/23.76; 424/424
(58) Field of Classification Search .................. None
See application file for complete search history.

(56) References Cited

U.S. PATENT DOCUMENTS

| | | | |
|---|---|---|---|
| 4,260,725 A | 4/1981 | Keogh et al. | |
| 4,680,268 A | 7/1987 | Clark, Jr. | |
| 4,970,145 A | 11/1990 | Bennetto et al. | |
| 5,741,319 A | 4/1998 | Woloszko et al. | |
| 5,741,330 A | 4/1998 | Brauker et al. | |
| 5,804,048 A | 9/1998 | Wong et al. | |
| 6,528,584 B2 | 3/2003 | Kennedy et al. | |
| 7,404,819 B1 | 7/2008 | Darios et al. | |
| 2003/0059631 A1 | 3/2003 | Al-Lamee | |

FOREIGN PATENT DOCUMENTS

| | | |
|---|---|---|
| WO | WO 98/38906 | 9/1998 |
| WO | 0013003 | 3/2000 |

OTHER PUBLICATIONS

Amato et al., Jun. 1989, Experience with the Polytetrafluoroethylene Surgical Membrane for Pericardial Closure in Operations for Congenital Cardiac Defects, J Thorac Cardiovasc Surg., 97(6): 929–934.

Copeland et al., Jun. 2001, Synthetic Membrane Neo–Pericardium Facilitates Total Artificial Heart Explanation, J Heart and Lung Transpl., 20(6): 654–656.

Gore Preclude® Pericardial Membrane Brochure, Jun. 2009, W.L. Gore & Associates, Inc., Flagstaff, AZ 86004.

Harada et al., Nov. 1988, Long–term Results of the Clinical Use of an Expanded Polytetrafluoroethylene Surgical Membrance as a Pericardial Substitute, J Thorac Cardiovasc Surg., 96(5): 811–815.

Heydorn et al., Aug. 1987, A New Look at Pericardial Substitutes, J Thorac Cardiovasc Surg., 94(2): 291–296.

(Continued)

*Primary Examiner* — Jeanne M Clark

(57) ABSTRACT

The present invention provides a biointerface membrane for use with an implantable device that interferes with the formation of a barrier cell layer including; a first domain distal to the implantantable device wherein the first domain supports tissue attachment and interferes with barrier cell layer formation and a second domain proximal to the implantable device wherein the second domain is resistant to cellular attachment and is impermeable to cells. In addition, the present invention provides sensors including the biointerface membrane, implantable devices including these sensors or biointerface membranes, and methods of monitoring glucose levels in a host utilizing the analyte detection implantable device of the invention. Other implantable devices which include the biointerface membrane of the present invention, such as devices for cell transplantation, drug delivery devices, and electrical signal delivery or measuring devices are also provided.

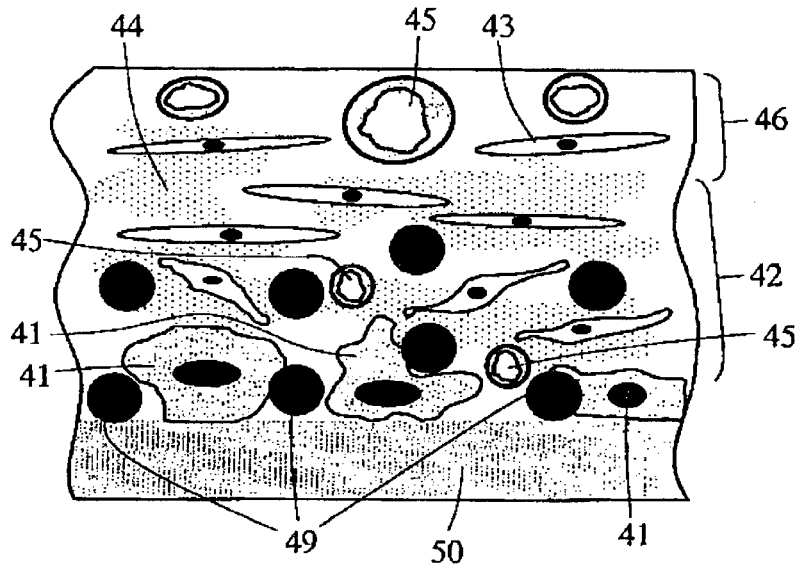

OTHER PUBLICATIONS

Leprince et al., Jan. 2001, Expanded Polytetrafluoroethylene Membranes to Wrap Surfaces of Circulatory Support Devices in Patients Undergoing Bridge to Heart Transplantation, Eu J Cardiothor Surg 19: 302–306.

Loebe et al., 1993, Use of Polytetrafluoroethylene Surgical Membrance as a Pericardial Substitute, PTFE Membrane in Correction of Congenital Heart Defects—Texas Heart Institute Journal 20(3): 213–217.

Minale et al., Sep. 1988, Clinical Experience with Expanded Plytetrafluoroethylene Gore–Tex® Surgical Membrane for Pericardial Closure: A Study of 110 Cases, J Card Surg., 3(3): 193–201.

PRECLUDE® Pericardial Membrane Brochure, Nov. 2001, W.L. Gore & Associates, Inc., Flagstaff, AZ 86004.

Revuelta et al., Mar. 1985, Expanded Polytetrafluoroethylene Surgical Membrane for Pericardial Closure, J Thorac Cardiovasc Surg., 89(3): 451–455.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2 and 13 is confirmed.

New claim 44 is added and determined to be patentable.

Claims 3-12 and 14-43 were not reexamined.

*44. A biointerface membrane according to claim 1, further comprising an enzyme membrane, wherein the enzyme membrane comprises an enzyme configured to react with glucose.*

\* \* \* \* \*

(12) EX PARTE REEXAMINATION CERTIFICATE (9725th)
United States Patent
Brauker et al.

(10) Number: US 6,702,857 C2
(45) Certificate Issued: Jun. 26, 2013

(54) MEMBRANE FOR USE WITH IMPLANTABLE DEVICES

(75) Inventors: James H. Brauker, San Diego, CA (US); Mark C. Shults, Madison, WI (US); Mark A. Tapsak, San Diego, CA (US)

(73) Assignee: Dexcom, Inc., San Diego, CA (US)

Reexamination Request:
No. 90/012,628, Sep. 14, 2012

Reexamination Certificate for:
Patent No.: 6,702,857
Issued: Mar. 9, 2004
Appl. No.: 09/916,386
Filed: Jul. 27, 2001

Reexamination Certificate C1 6,702,857 issued Jul. 26, 2011

(51) Int. Cl.
*A61F 2/02* (2006.01)
*C07K 14/78* (2006.01)
*A61F 2/00* (2006.01)

(52) U.S. Cl.
USPC ........................................ 623/23.76; 424/424

(58) Field of Classification Search
None
See application file for complete search history.

(56) References Cited

To view the complete listing of prior art documents cited during the proceeding for Reexamination Control Number 90/012,628, please refer to the USPTO's public Patent Application Information Retrieval (PAIR) system under the Display References tab.

*Primary Examiner* — Beverly M. Flanagan

(57) ABSTRACT

The present invention provides a biointerface membrane for use with an implantable device that interferes with the formation of a barrier cell layer including; a first domain distal to the implantantable device wherein the first domain supports tissue attachment and interferes with barrier cell layer formation and a second domain proximal to the implantable device wherein the second domain is resistant to cellular attachment and is impermeable to cells. In addition, the present invention provides sensors including the biointerface membrane, implantable devices including these sensors or biointerface membranes, and methods of monitoring glucose levels in a host utilizing the analyte detection implantable device of the invention. Other implantable devices which include the biointerface membrane of the present invention, such as devices for cell transplantation, drug delivery devices, and electrical signal delivery or measuring devices are also provided.

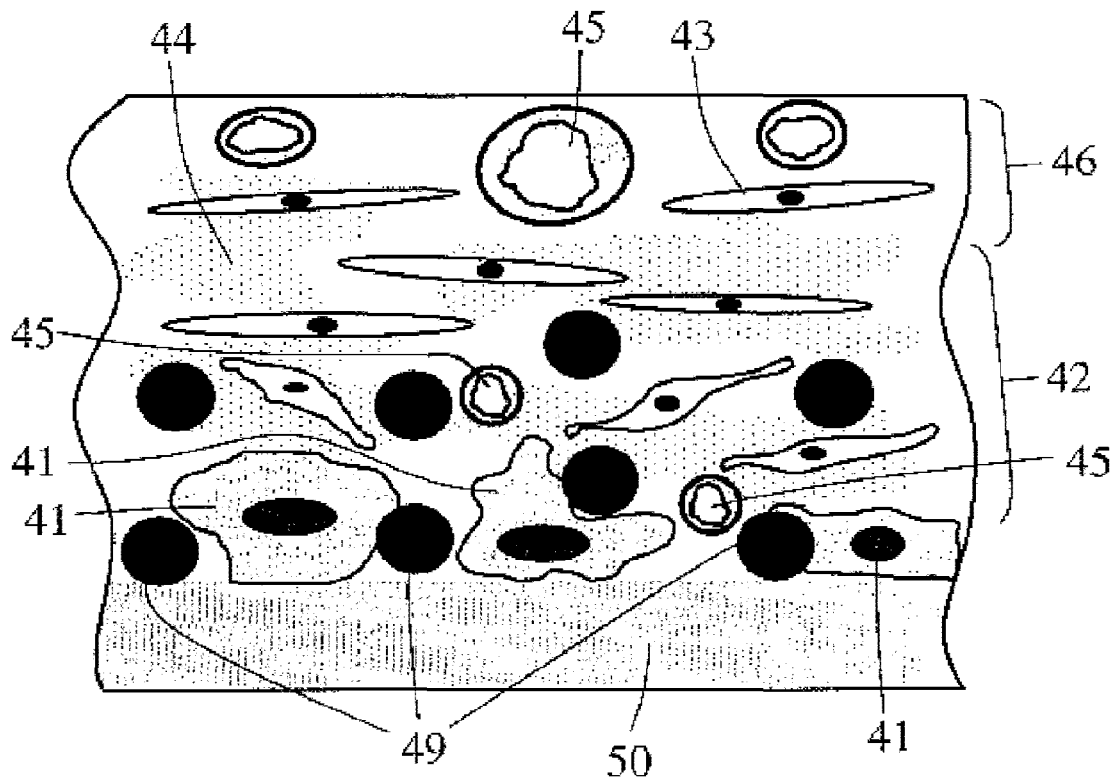

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-11, 23-42 and 44 is confirmed.

Claim 43 is determined to be patentable as amended.

New claims 45-50 are added and determined to be patentable.

Claims 12-22 were not reexamined.

43. A biointerface membrane comprising a first domain and a second domain in combination that are adapted to:
 a) permit tissue ingrowth into said first domain;
 b) interfere with barrier cell formation on or within said first domain;
 c) resist [baffler] *barrier* cell attachment to said second domain; and
 d) block cell penetration into said second domain.

*45. The biointerface membrane according to claim 1, wherein the second domain is configured to contact a biological fluid.*

*46. The biointerface membrane according to claim 42, wherein the second domain is adapted to contact a biological fluid.*

*47. The biointerface membrane according to claim 43, wherein the second domain is adapted to contact a biological fluid.*

*48. The biointerface membrane according to claim 1, wherein the second domain is adjacent to the first domain.*

*49. The biointerface membrane according to claim 42, wherein the second domain is adjacent to the first domain.*

*50. The biointerface membrane according to claim 43, wherein the second domain is adjacent to the first domain.*

\* \* \* \* \*